United States Patent
Mizoguchi et al.

(10) Patent No.: US 9,448,204 B2
(45) Date of Patent: Sep. 20, 2016

(54) MAGNETIC IMMUNOASSAY USING AC SUSCEPTIBILITY MEASUREMENT

(71) Applicant: Hitachi, Ltd., Chiyoda-ku, Tokyo (JP)

(72) Inventors: Takako Mizoguchi, Sayama (JP);
Ryuzo Kawabata, Higashiyamato (JP);
Akihiko Kandori, Tokyo (JP)

(73) Assignee: HITACHI, LTD., Tokyo (JP)

( * ) Notice: Subject to any disclaimer, the term of this patent is extended or adjusted under 35 U.S.C. 154(b) by 211 days.

(21) Appl. No.: 13/803,632

(22) Filed: Mar. 14, 2013

(65) Prior Publication Data

US 2013/0288384 A1    Oct. 31, 2013

(30) Foreign Application Priority Data

Apr. 26, 2012  (JP) ................. 2012-100548

(51) Int. Cl.
*G01N 33/543*  (2006.01)
*G01N 27/72*  (2006.01)

(52) U.S. Cl.
CPC ........ *G01N 27/72* (2013.01); *G01N 33/54333* (2013.01)

(58) Field of Classification Search
CPC ............................ G01N 27/745; G01N 27/72
USPC .................................................. 436/518, 526
See application file for complete search history.

(56) References Cited

U.S. PATENT DOCUMENTS

| | | | |
|---|---|---|---|
| 5,445,970 A | | 8/1995 | Rohr |
| 5,445,971 A | * | 8/1995 | Rohr ............................ 436/526 |
| 6,150,182 A | * | 11/2000 | Cassaday ..................... 436/526 |
| 2013/0121879 A1 | | 5/2013 | Kawabata et al. |

FOREIGN PATENT DOCUMENTS

| | | |
|---|---|---|
| JP | H07-504986 A | 6/1995 |
| JP | 2001-33455 | 2/2001 |
| WO | WO 2012/011477 A1 | 1/2012 |

OTHER PUBLICATIONS

Keiji Enpuku et al, detection of Magnetic Nanoparticles with Superconducting Quantum Interference Device (SQUID) Magnetometer and Application to Immunoassays, Japanese journal of Applied Physics, Oct. 1, 1999, vol. 38, Part 2, No. 10.
Y. R.. Chemla et al, Ultrasensitive magnetic biosensor for homogeneous immunoassay, PNAS, Dec. 19, 2000, vol. 97, No. 26.
R. Kotitz et al., SQUID Based Remanence Measurements for Immunoassays, IEEE Transactions on Applied Superconductivity, Jun. 1997, vol. 7, No. 2.
Ryuzo Kawabata et al, Immunoassay Detection without Washing by Using AC Magnetic Susceptibility, IEEE Sensors 2010 Conference.

* cited by examiner

*Primary Examiner* — Mark Shibuya
*Assistant Examiner* — Pensee Do
(74) *Attorney, Agent, or Firm* — Baker Botts L.L.P.

(57) ABSTRACT

In a magnetic immunoassay using AC magnetic susceptibility measurement, a signal from non-coupled magnetic particles is prevented to mix with a desired measurement signal from magnetic particles coupled with an object to be measured. A sample vessel in which a mixed solution of an inspection objective sample and the magnetic particles are included is carried by a sample support, such that a precipitation of the magnetic particle coupled with the object to be measured dispersed in the solution by a magnetic field from a dissociating coil is promoted. Next, the sample vessel is carried to the magnetizing coil and the magnetic signal from the non-coupled magnetic particle remaining in a supernatant in the vessel is peculiarly measured by an MR sensor to perform AC magnetic susceptibility measurement with high precision.

10 Claims, 6 Drawing Sheets

MAGNETIC IMMUNOASSAY USING AC SUSCEPTIBILITY MEASUREMENT

CLAIM OF PRIORITY

The present application claims priority from Japanese patent application JP 2012-100548 filed on Apr. 26, 2012, the content of which is hereby incorporated by reference into this application.

BACKGROUND OF THE INVENTION

1. Field of the Invention

The present invention relates to a technology of measuring a magnetic particle quantity included in a liquid using a magnetic sensor, and more particularly, to an immunoassay measuring technology of measuring a protein, such as an antigen, an antibody, a tumor marker, a cell component or a very small quantity of hormone material, and the like.

2. Description of the Related Arts

Recently, an immunological measuring method (Patent Document 1: see Japanese Patent Application Laid-Open Publication (JP-A) No. 2001-33455) that is based on an antigen-antibody reaction as a principle is mainly used for inspection items, such as allergy, infectious disease, tumor marker, thyroid hormone, and the like. As the immunological measuring method, there are various highly sensitive measurement methods, such as a radio immunoassay (RIA) using a radioisotope, an enzyme immunoassay (EIA) using an enzyme, and a chemiluminescent enzyme immunoassay (CLEIA) combining an enzyme and chemiluminescent substrate. Meanwhile, for the highly sensitive immunological measuring method, tubidimetric immunoassays have been frequently used in view of handling easiness. The turbidimetric immunoassays are a method that uses one to several kinds of antibodies and detects an object to be measured based on an antigen-antibody reaction sandwiching an antigen with the antibodies and a change in turbidity or transmittance of a solution in supernatant as an index after precipitating composites generated by the reaction. These optical methods measure turbidity or coloring of a solution and a change in a very small quantity of fluorescent and luminescent materials to detect the object to be measured. These methods generally require a process (bound/free separation) of cleaning non-coupled markers occurring during the reaction process, which leads to complexity of a working process. Further, when there is turbidity or coloring in a reaction solution, there is a problem in that the detection precision may be degraded.

An example for addressing the problem may include the magnetic measuring technology. The magnetic measurement means a method of detecting a magnetic particle coupled with the object to be measured using a magnetic sensor. As the method, a magnetic susceptibility measurement, a residual magnetism measurement, and the like, due to the difference in a measurement principle of a magnetic particle have been reported (see Non-Patent Document 1: K. Enpuku et al. Jpn. J. Appl. Phys. 38, p. L1102 (1999), Non-Patent Document 2: Y. R. Chemla et al. Proc. Nat 1. Acad. Sci. USA 97, p. 14268 (2000), and Non-Patent Document 3: R. Koetitz et al. IEEE Trans. App 1. Supercond. 7, p. 3678 (1997)). Further, an AC magnetic susceptibility measurement method of measuring a quantity of surplus magnetic particles, which are not coupled with the object to be measured, as magnetic signals is disclosed in Non-Patent Document 4 (R. Kawabata et al. IEEE Sensors Conference (2010)). For the immunoassay such as ELISA, and the like, a process of cleaning and removing surplus markers, and the like, which are not coupled with the object to be measured, is required, but the method disclosed in Non-Patent Document 4 does not require a cleaning process and therefore can implement a fast measurement. In addition, since the method does not require cooling of a magnetic sensor or a magnetic film, a configuration of an apparatus can be simplified.

SUMMARY OF THE INVENTION

The method of measuring AC magnetic susceptibility is divided into the following two steps. First, a sample is mixed with marker immobilized magnetic particles. The marker is antigen, antibody, ligand, or the like, that bind specifically to the object to be measured. Second, the mixed solution is magnetized with an AC magnetic field. Then the object to be measured can be quantified by measuring the magnetic signal emitted from the magnetic particle. Generally, in the second step, only the signal emitted from the magnetic particle that is not coupled with the object to be measured may be detected since the magnetic particle may have a short Brown relaxation time and follow up a magnetizing magnetic field. Meanwhile, since the magnetic particle coupled with the object to be measured has a long Brown relaxation time, the signal is not detected.

As the magnetic particle, an iron oxide-based ferrite particle may be mainly used and in order to more increase the magnetic susceptibility, particles including cobalt, nickel, and the like may be used. As more preferable characteristics of a particle, a particle having strong residual magnetic characteristics while having a particle size of several tens to 200 nm may be used.

The reason is that a magnetic moment of the magnetic material leads to the Brown relaxation of the magnetic particle, and thus the magnetic moment may effectively follow up a magnetizing AC magnetic field and a high magnetic signal may be shown. However, the magnetic particle having strong residual magnetism may have a poor dispersibility and may be easily agglomerated to make it difficult to be handled. Meanwhile, the magnetic particle having superparamagnetism may have a good dispersibility and may be easily handled, but when the particle size of the magnetic particle is small, the magnetic particle has the magnetic moment leading to Neel relaxation in many cases. In the case of the magnetic particle having the magnetic moment leading to Neel relaxation, the high magnetic signal is radiated even in the particle that does not follow up the excited AC magnetic field. For this reason, the measurement precision is remarkably reduced by detecting a magnetic signal component emitted from the non-coupled magnetic particle and the magnetic signal component emitted from the coupled magnetic particle.

As described above, when using the magnetic particle having the excellent superparamagnetism characteristic in terms of dispersibility, there are problems in that the signal is detected even from the magnetic particle coupled with the object to be measured and the detection precision of the AC magnetic susceptibility measurement method using the difference in the Brown relaxation time may be reduced. Therefore, an object of the present invention is to provide a magnetic immunoassay method and apparatus that suppress a mixing of a magnetic signal from a magnetic particle coupled with the object to be measured in a magnetic immunoassay using an AC magnetic susceptibility measurement, thereby mitigating a limitation of the used magnetic particles and keeping a high measurement precision.

An immunoassay method according to a representative embodiment of the present invention can precipitate magnetic particles coupled with the object to be measured and measure non-coupled magnetic particles remaining in a supernatant, thereby widening a limitation of the used magnetic particles and measuring AC magnetic susceptibility with high precision. In more detail, in the magnetic immunoassay method according to the present invention mixes and couples and reacts a sample solution with an already known quantity of magnetic particles fixing an antigen, an antibody, or a ligand peculiarly coupled with the object to be measured in a non-magnetic sample vessel. Next, the magnetic immunoassay method precipitates the magnetic particles coupled with each other via the object to be measured, installs the sample vessel under the AC magnetic field to excite the sample solution, and detects the magnetic signal component emitted from the magnetic particle floating in the non-coupled state in the sample solution to classify or quantify the object to be measured remaining in the sample solution.

In detail, prior to magnetizing the objective sample solution and performing the magnetic signal measurement, the excitation and the magnetic signal measurement are performed on a control sample including the magnetic particle of the same quantity as one added to the sample solution and not including the object to be measured. Since conditions other than presence and absence of the object to be measured are the same, the same magnetizing coil as one used for the magnetization of the objective sample solution and the magnetic signal measurement and the magnetic sensor are used and a kind of the sample vessel, a quantity of a solution, a positional relationship with the magnetic sensor, and the like are the same at the time of the excitation of the objective sample solution and the magnetic signal measurement. Therefore, when the magnetic signal strength from the obtained control sample is set to be $B0$ and the magnetic signal strength obtained from the excitation of the objective sample solution and the magnetic signal measurement, which are performed subsequently, is set to be B, a quantity of the object to be measured in the sample solution may be determined from a change rate $\alpha=\{1-B/B0\}\times100[\%]$ of the magnetic signal strength.

Describing in more detail, in order to overcome a change in a coupling efficiency occurring due to a kind of antibody or ligand used for peculiar coupling with the object to be measured and a difference in a manufacturing lot of the antibody or the ligand, and the like, and a resultant change in detection sensitivity, a calibration curve method is applied. That is, calibration curves are acquired for each kind of the used antibody or the ligand, each manufacturing lot, or every time the other measurement conditions are changed and a content of the object to be measured corresponding to the change rage a, which is obtained from the magnetic signal strengths B and $B0$ obtained at the time of the measurement of the objective sample solution as described above, is read from the calibration curve, thereby determining the quantity of the object to be measured contained in the measured sample solution.

Herein, the used calibration curve is acquired as follows. First, a plurality of standard samples each containing each of standard quantities of the object to be and aforementioned already known quantity of magnetic particles are prepared. The standard quantities are dispersed in a range of assumed quantity of the object to be measured. The same control sample as the foregoing one including only the magnetic particles but not including the object to be measured and the plurality of standard samples are sequentially provided to the same process as the foregoing process of magnetizing and precipitating the sample solution and measuring the magnetic signal. Change rates $\alpha n=\{1-Bn/B0\}\times100[\%]$ (n=1, 2, 3, . . . ) of the magnetic signal strength $B0$ obtained at the time of the magnetic signal measurement of the control sample and a magnetic signal strength Bn (n= 1, 2, 3, . . . ) obtained at the time of the magnetic signal measurement of each standard sample are each obtained. Values of the change rate $\alpha n$ (n=1, 2, 3, . . . ) obtained as described above are plotted on a two-dimensional plane of which the horizontal axis indicates the content of the object to be measured and the plotted points are connected or the line is further subjected to smoothing processing to obtain the calibration curve.

The subject matter of the AC magnetic susceptibility measurement adopted in the magnetic immunoassay method according to the present invention is to suppress the mixing of the magnetic signal from the magnetic particle coupled with the object to be measured and accurately detect the magnetic signal component indicating the quantity of the magnetic particles remaining in the solution due to the non-coupling. In order to promote dissociation due to the agglomeration and the precipitation, it is effective to apply a dissociating magnetic field (AC magnetic field or DC magnetic field). Further, as the immunoassay apparatus, a device for adopting an longitudinal tube-shaped reacting vessel, a device for adopting a magnetic sensor having local sensitivity, and a device for including an equipment of freely adjusting a mutual position between the sample vessel and the magnetic sensor are effective so as to easily detect the magnetic signal of a supernatant portion while avoiding an effect of the magnetic signal from the precipitated agglomerates.

Further, a concept of the present invention also includes a configuration of putting, in the sample solution, immobilized beads fixing a second antibody, an antigen, or a ligand, that is to bind peculiarly to the object to be measured, as well as the magnetic particles fixing an antibody, an antigen, or a ligand that is also to bind peculiarly to the object to be measured, and coupling the magnetic particle with the immobilized beads in the sample solution by a sandwich reaction sandwiching the object to be measured. As the immobilized beads, it is necessary to select a material, and the like that are once dispersed in the solution and thus is in a suspension state and is also agglomerated by the coupling with the magnetic particles so as to be quickly precipitated. Elements such as a size of the carrier, a specific gravity or a hydrophilic property of a material, and the like affect these properties. Representatively, the polystyrene bead is appropriate as the carrier.

As another modification, a modification of using the reaction vessel of which a part of the inner surface is used as a surface fixing an antigen or an antibody that is to bind peculiarly to the object to be measured may also be allowed. In this case, a reaction of agglomerating the magnetic particles in the sample solution on a wall surface of the sample vessel via the object to be measured is generated. Therefore, the quantity of the magnetic particles remaining in the solution is measured by detecting the magnetic signal of the sample solution after the reaction under the AC magnetic field and the object to be measured remaining in the sample solution may be classified or quantified based on the measured quantity of the magnetic particles. Even in the modification, in terms of avoiding the mixing of the magnetic signal from the magnetic particles coupled and deposited on the wall surface, it is effective to locally limit a surface fixing an antigen or an antibody that is to bind peculiarly to the object to be measured to the vicinity of a bottom of the reaction vessel, and the like, and to perform the magnetic measurement, avoiding the surface.

According to an aspect of the present invention, even in using the magnetic particles having high superparamagnetism characteristics, the mixing of the signal component from the magnetic particle coupled with the object to be measured may be reduced without performing the cleaning process, such that the AC magnetic susceptibility measurement method with high precision may be realized.

DETAILED DESCRIPTION OF THE PREFERRED EMBODIMENTS

First Embodiment

Figure 1:
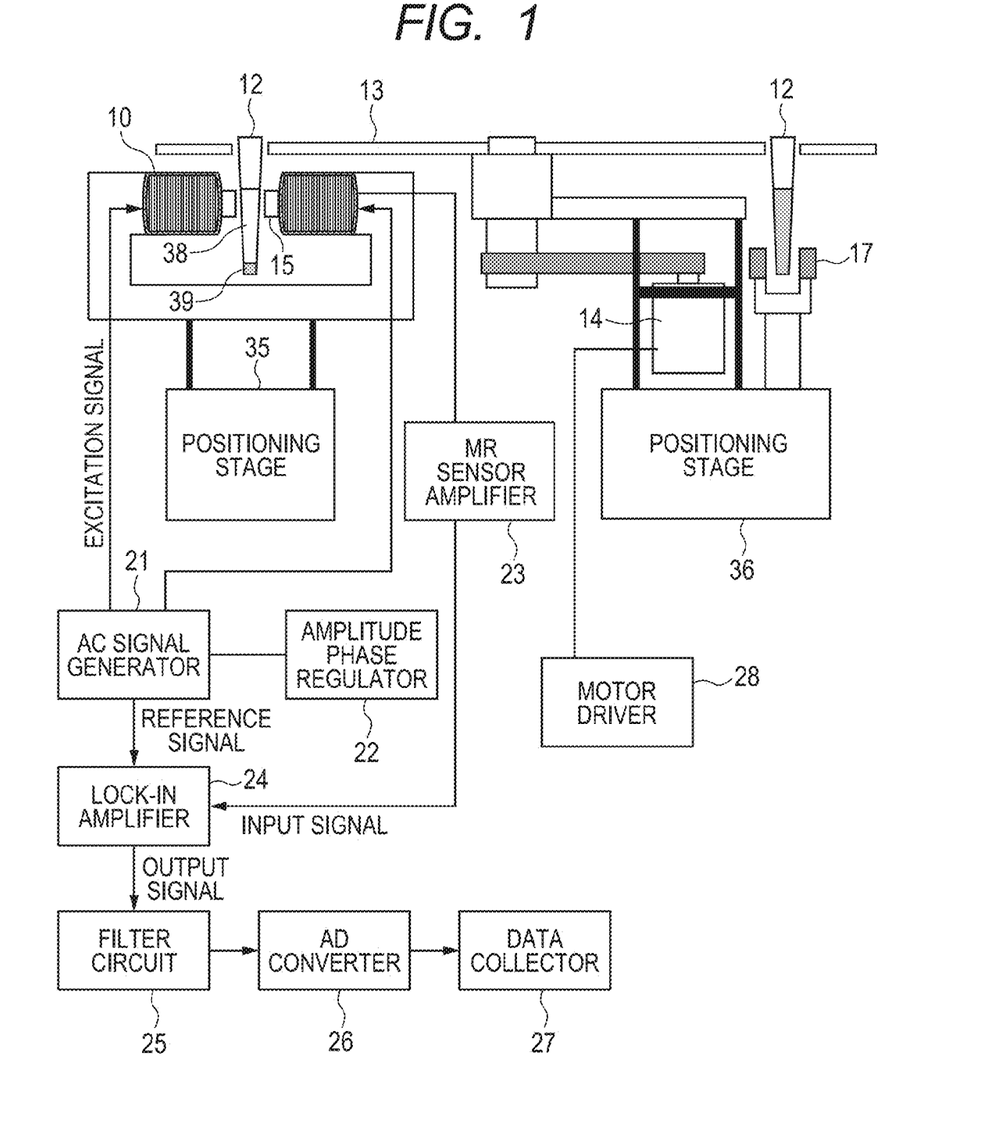
FIG. 1 is a block diagram illustrating a configuration an immunoassay apparatus according to an embodiment of the present invention.

An immunoassay apparatus used in a first embodiment of the present invention has an apparatus configuration as illustrated in FIG. 1. A main configuration is as follows.

A magnetizing coil 10 for magnetizing magnetic particles is wound around a U-shaped core and is driven by an AC signal generator 21. An inspection sample is put in a sample vessel 12 that is mounted on a circumference of a disk-shaped sample support 13. The sample support 13 rotatably moves by a DC motor 14. The motor drive 28 drives the DC motor 14 and controls a rotation thereof. The arranged sample vessel 12 is first mounted at a position of a coil 17 applying a dissociating magnetic field by the rotation of the sample support 13 and then is mounted in a cap of the core of the magnetizing coil 10.

The cap of the core of the magnetizing coil 10 is provided with magnetic resistance effect element (MR sensor) 15 and when the same cap is mounted with the sample vessel 12, the magnetic particle within the vessel is magnetized by AC magnetism emitted from the magnetizing coil 10 to detect a magnetic signal from the magnetic particle. In detail, the element output of the MR sensor 15 is amplified with an MR sensor amplifier 23 and synchronously detected with a lock-in amplifier 24. A reference signal for synchronous detection is given from the AC signal generator 21 controlled with an amplitude phase regulator 22. The output signal obtained by the synchronous detection is stored in a data collector 27 via a filter circuit 25 and an AD converter 26. Therefore, a dispersive waveform having a minimum value and a maximum value may be obtained. A difference (peak-to-peak strength) between the maximum value and the minimum value in the dispersive waveform is the magnetic signal strength generated from the magnetic particle.

The reaction occurring in the sample vessel 12 will be described in detail with reference to FIG. 2. The sample solution that is an inspection object is added with the immobilized beads and the magnetic particle to prepare a sample solution for measurement. An object to be measured 1 that is an object of quantification or classification is, for example, an antigen. A magnetic particle 4 is fixed with a first antibody 41 peculiarly coupled with the antigen. Further, a surface of immobilized beads 3 is fixed with a second antibody 43 that is to bind peculiarly to the object to be measured 1. Herein, a quantity of the magnetic particle 4 added is converted into the quantity of the first antibody 41 that is also to bind peculiarly to the object to be measured 1 in the sample solution, which corresponds to an assumed maximum quantity of the object to be measured or is a defined more surplus quantity. In addition, the quantity of the immobilized beads 3 is a quantity sufficient to couple all the magnetic particles 4 in the sample solution via the object to be measured. That is, a quantity of the immobilized beads 3 added is converted into the fixed quantity of the second antibody 43 and a quantity corresponding to an added quantity (however, this is a fixed quantity of the first antibody 41) of the magnetic particle 4 or a more surplus quantity.

Figure 2:
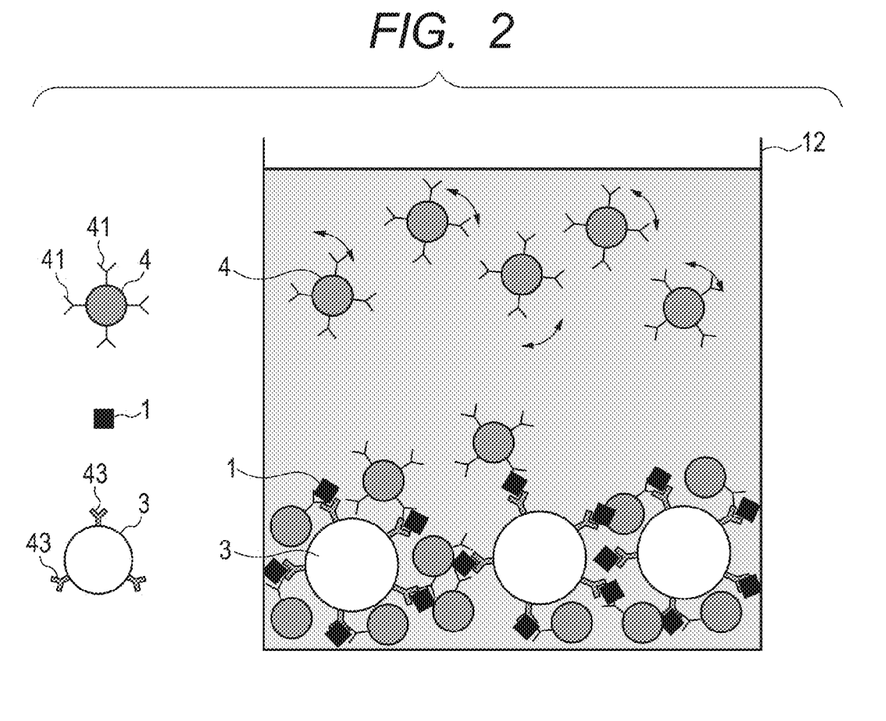
FIG. 2 is a schematic diagram illustrating a reaction within a sample vessel according to the embodiment.

When the sample solution is agitated and is placed for a sufficient time, the sample solution is in a state illustrated in FIG. 2. The antigen 1 that is the object to be measured is coupled with the first antibody 41 fixed to the magnetic particle 4 and the antibody 43 fixed to the immobilized beads 3. Therefore, a conjugate of the magnetic particle and the immobilized beads are generated. The conjugate is agglomerated and precipitated at the bottom of the vessel 12. Meanwhile, the magnetic particle that is not coupled with the antigen remains in the sample solution. As described above, the conjugate of the magnetic particle and the immobilized beads and the non-coupled magnetic particle are mixed in the sample solution.

In this case, the non-coupled magnetic particle randomly moves and rotatably moves in the sample solution and the magnetic susceptibility of the magnetic particle is exponentially attenuated over time. This phenomenon is called Brown relaxation and is in proportion to a volume of the magnetic particle and the relaxation time τ is represented by τ=3 ηV/kBT (η represents a viscosity of an inspection solution, V represents a volume of a magnetic particle, kB represents a Boltsmann's constant, and T represents a temperature). In addition, the volume V is represented by V=(π/6) d3 by a diameter d of the magnetic particle. Here, when a diameter of the conjugate of the magnetic particle having a diameter of 0.1 microns and a polystyrene carrier having a diameter of 3.2 microns is set to be 3.3 μm, the relaxation time τB is 14 seconds. Meanwhile, in the magnetic particle having a diameter of 0.1 microns, the relaxation time τB is 0.4 mm seconds and is very small as about 1/3000 of the relaxation time of the conjugate. In the state in which the conjugate and the non-coupled magnetic particle are mixed in the same sample solution, a magnetic signal component can be extracted from the non-coupled magnetic particle by using the difference in the Brown relaxation time of the conjugate and the magnetic particle. Further, when using the measurement result of the control sample that does not include the object to be measured and is added with a defined quantity of magnetic particle similar to the objective sample, the quantity of the coupled magnetic particle, that is, the quantity of the object to be measured included in the objective sample may be calculated by a change rate of the magnetic signal output from the objective sample, based on the magnetic signal output from the control sample. However, when the magnetic particle has a strong superparamagnetism characteristic, the magnetic signal causing Neel relaxation of the magnetic particle included in the conjugate is generated. For this reason, the foregoing change rate may be detected as a value lower than an actual value. Therefore, the immunoassay apparatus of the present embodiment adopts a configuration of suppressing the mixing of the magnetic signal from the magnetic particle coupled with the object to be measured so that an error is not generated in the quantifying of the negative measuring material.

Figure 3:
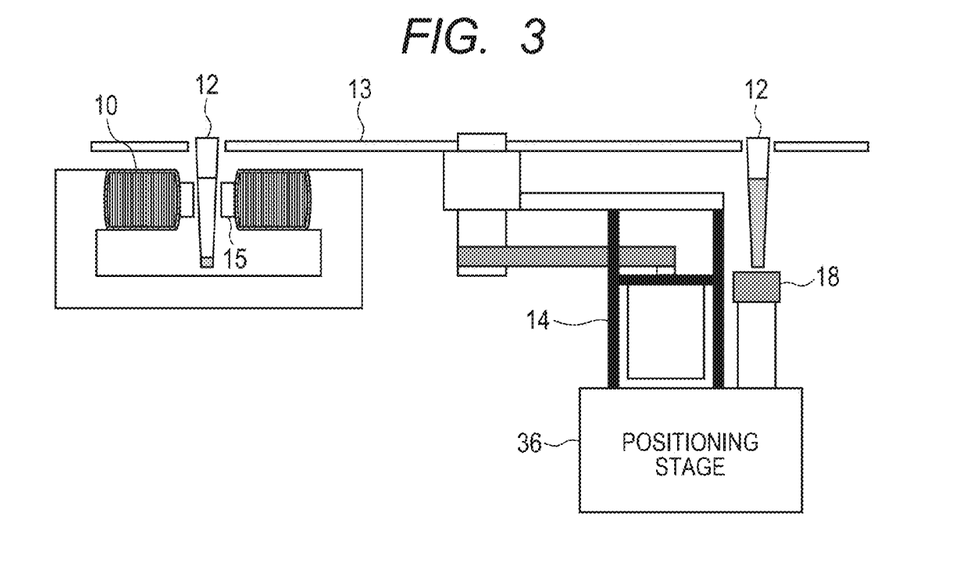
FIG. 3 is a block diagram illustrating main components of an immunoassay apparatus in which a dissociating member of the coupled magnetic particles is modified.

A detailed operation of the immunoassay apparatus of the embodiment will be continuously described with reference to FIG. 1. The sample vessel 12 in which the immobilized beads and the magnetic particle are added to the sample solution and agitated is disposed on the sample support 13 and moves to a position of the dissociating coil 17 generating the dissociating AC magnetic field by the rotation of the sample support 13. The dissociating magnetic field serves to promote the agglomeration and precipitation of the immobilized beads 3 dispersed in the solution. The magnetic field strength may be appropriately about 1 to 5 mT. When the magnetic field higher than needs is applied, a problem of agglomerating even the magnetic particle remaining in the solution without being coupled with the antigen may occur. Further, a configuration of the apparatus may be modified to apply the AC magnetic field, instead of the AC magnetic field from the dissociating coil 17. FIG. 3 illustrates main components of the modified immunoassay apparatus. Instead of the dissociating coil 17 of the apparatus of FIG. 1, a permanent magnet 18 is attached to an arm of a positioning stage 36. Therefore, the sample vessel 12 receives the DC magnetic field from the bottom.

The sample vessel 12 receives the magnetic field for agglomeration and precipitation at the position of the dissociating coil 17 and then moves to the position of the magnetizing coil 10 and as described above, the magnetic signal of the magnetic particle floating in the solution due to the non-coupling is detected by the MR sensor 15. In detail, the magnetizing coil 10 and the MR sensor 15 are previously adjusted by the positioning stages 35 and 36 so as to be disposed at a height corresponding to a supernatant 38 inside the sample vessel 12. Therefore, the mixing of the magnetic signal component from the conjugate 39 of the immobilized beads and the magnetic particle precipitated in the bottom of the sample vessel 12 is suppressed. The necessity of the suppression of the magnetic signal component from the coupled magnetic particle and the modified configuration therefor will be described below. Next, a sequence of a representative magnetic immunoassay method using the immunoassay apparatus of the present embodiment will be described.

In the magnetic immunoassay method of the embodiment, in order to overcome a change in a coupling efficiency occurring due to a kind of antibody or ligand used for peculiar coupling with the object to be measured and a difference in a manufacturing lot of the antibody or the ligand, and the like, or a change in detection sensitivity due to a change in various conditions, a calibration curve method is applied.

Figure 4:
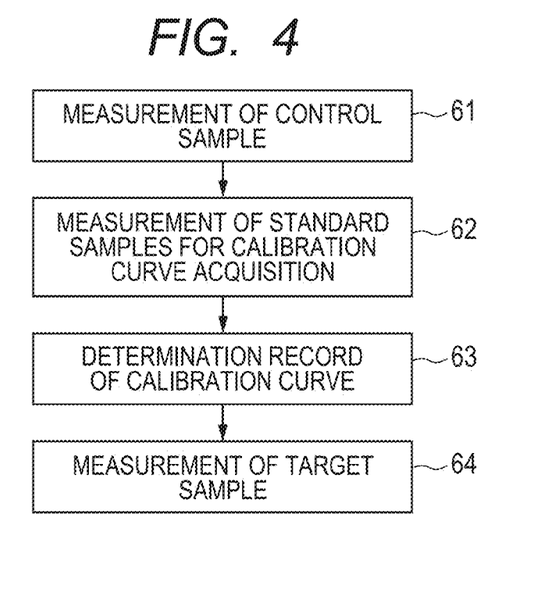
FIG. 4 is a flow chart illustrating a sequence of an immunoassay method performed in the embodiment.

The flow chart of FIG. 4 will be described. The magnetic immunoassay method of the present embodiment is performed in a sequence of measuring a control sample in a first step 61, measuring a plurality of standard samples in a second step 62, determining and recording a calibration curve in a third step 63, and measuring the objective sample in a fourth step 64. The first to third steps are performed for each kind of used antibody or ligand, each manufacturing lot, or every time the other measuring conditions are changed. The control sample is a sample to which a defined quantity of magnetic particle is added or in which a quantity of a solution is adjusted to a defined value within the sample vessel. Further, the plurality of standard samples measured in the second step 62 are samples respectively containing the object to be measured of standard quantities respectively. The standard quantities covers the range of the assumed quantity of the object to be measured. Each of the standard samples is added with the foregoing defined quantity of magnetic particle, and is obtained by adjusting the quantity within the sample vessel to a predetermined quantity.

Figure 5A:
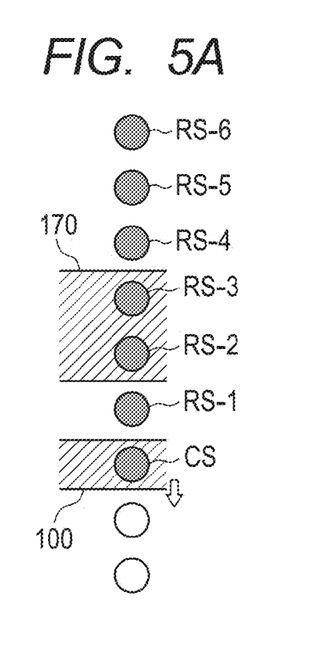
FIG. 5A is a conceptual diagram illustrating a state in which the sample vessels are arranged and sequentially measured in the embodiment.
Figure 5B:
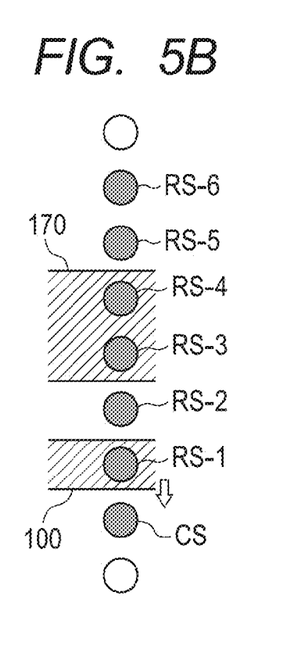
FIG. 5B is a conceptual diagram illustrating a state in which the sample vessels are arranged and sequentially measured in the embodiment.
Figure 5C:
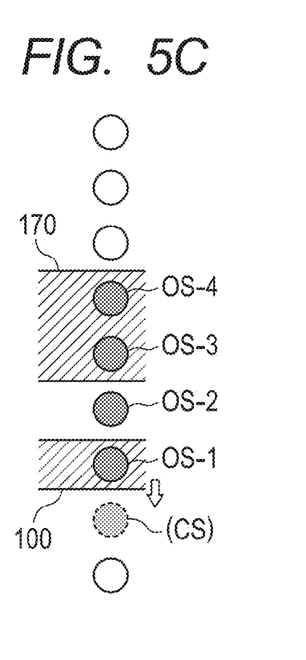
FIG. 5C is a conceptual diagram illustrating a state in which the sample vessels are arranged and sequentially measured in the embodiment.

FIGS. 5A-5C illustrate the state in which the adjusted sample vessel is disposed on the sample support 13 and the samples are sequentially provided in a process for dissociation and a process for excitation and magnetic measurement. Actually, the sample vessel moves along the circumference by the disk-shaped sample support 13, but FIGS. 5A-5C illustrate that the sample vessel vertically moves for convenience. FIG. 5A illustrates that a leading control sample CS in the arranged samples delivers a measuring region 100, that is, a region to which the magnetizing magnetic field from the coil 10 is applied and in this region, the magnetic measurement is performed. Standard samples RS-1 RS-2, RS-3, RS-4, . . . are sequentially arranged at a rear of the arrangement and the standard samples RS-2 and RS-3 among those samples are in a region to which the dissociating magnetic field is applied from a dissociating region 170, that is, the coil 17. When the measurement is completed, the whole sample support moves by one frame and thus is in a state of FIG. 5B. That is, the standard sample RS-1 moves to the measuring region and is subjected to the magnetic measurement. Next, the sample support 13 moves by one frame to perform the sequential measurement, such that the measurement of the control sample of the first step 61 and the measurement of the plurality of standard samples of the second step 62 are performed. When the measurement is completed by being performed only once, the control sample CS and the standard sample pass through the measuring region 100 once and then may be removed from the sample support. In addition, in order to improve an S/N ratio by performing the addition average processing of a plurality of signals, it is also effective to perform measurement by rotating the sample support 13 on which the control sample CS and the standard sample are mounted 5 to 10 times or more and passing the sample support 13 through the measuring region 100 plural times.

Next, in the third step 63, the magnetic signal strength obtained at the time of the magnetic measurement of the control sample CS is set to be B0 and the magnetic signal strength obtained at the time of the magnetic signal measurement of each standard sample RS-n (n=1, 2, 3, is set to be Bn (n=1, 2, 3, . . . ) and the change rate αn (n= 1, 2, 3, . . . ) is obtained by the sequence (Equation 1) from the B0 of the value of Bn.

$$\alpha n=\{1-Bn/B0\}\times 100[\%] \ (n=1,2,3,\ldots) \quad \text{(Equation 1)}$$

Further, values of the change rate αn (n=1, 2, 3, . . . ) obtained as described above are plotted on a two-dimensional plane of which the horizontal axis indicates the content of the object to be measured and the plotted points are connected or the line is further subjected to the smoothing processing, thereby obtaining a calibration curve. The example of the obtained calibration curve is illustrated in FIGS. 5A-5C.

Next, in the fourth step 64, the objective sample is prepared and measured. Each sample that is a control of the inspection is added with the defined quantity of magnetic particle, and the objective sample adjusted to the same defined quantity as described above is prepared and is arranged on the sample support 13. The plurality of objective samples, such as the sample from the plurality of portions, the sample from the plurality of test objects, and the like, may be arranged and sequentially measured. FIG. 4C illustrates the state in which objective samples OS-1, OS-2, OS-3, and OS-4 are arranged and the leading OS-1 reaches the measuring region and is measured. The magnetic signal strength obtained by measuring each objective sample is set to be B and the change rate α of the value of B for the magnetic signal strength B0 of the control sample acquired in the first step is obtained from (Equation 2).

$$\alpha=\{1-B/B0\}\times 100[\%] \quad \text{(Equation 2)}$$

The quantity of the object to be measured remaining in the sample solution of the objective sample is determined from the value of the change rate α and the previously determined calibration curve. As described above, the fourth step ends.

In addition, in the description of the foregoing sequence, for the calculation of the change rate based on Equation 2 in the fourth step, the magnetic measurement signal strength B0 of the control sample acquired in the first step is used. However, when the environmental conditions, and the like, of the measurement in the first and second steps and the fourth step to obtain the calibration curve are changed, prior to the measurement of the objective sample in the fourth step, the control sample may be adjusted again to perform the measurement and the value of the magnetic measurement signal B0 may be acquired. That is, as illustrated by the dashed line in FIG. 5C, in the front of the arrangement of a series of objective samples OS-1, OS-2, OS-3, and OS-4, the control sample CS is arranged and the value of the magnetic measurement signal B0 used to calculate the change rate of Equation 2 is measured at the time of measuring a series of the objective samples. Even in this case, the calibration curve itself obtained from the measurement of the first to second steps may be used as it is, regardless of the change in the detection sensitivity due to the change in the environmental conditions.

Modified Embodiment

In the foregoing embodiment, the object to be measured was an antigen and the conjugate fixed to the magnetic particle and the immobilized beads to be peculiarly coupled with the antigen was an antibody. The measured material may be an antibody and the conjugate fixed to the magnetic particle and the immobilized beads may be an antigen. Further, the modification can be made by the coupling reaction of the magnetic particle and the immobilized beads using another peculiar and selective coupling. Representatively, a configuration of fixing the ligands each coupled with acceptors included in the object to be measured as the conjugate to the magnetic particle and the immobilized beads may also be adopted. In addition, when the object to be measured is biotin, or the biotin is coupled as a mark with the object to be measured, the magnetic particle and the immobilized beads fixed with avidin or streptavidin as a conjugate may be adopted.

Further, in the embodiment, as the sandwich reaction sandwiching the object to be measured in the solution, the reacted magnetic particle was dissociated from the non-reacted magnetic particle using the reaction of coupling the magnetic particle with the immobilized beads. The dissociating mechanism different from the dissociating mechanism using the immobilized beads may also be used in the present invention.

Figure 6:
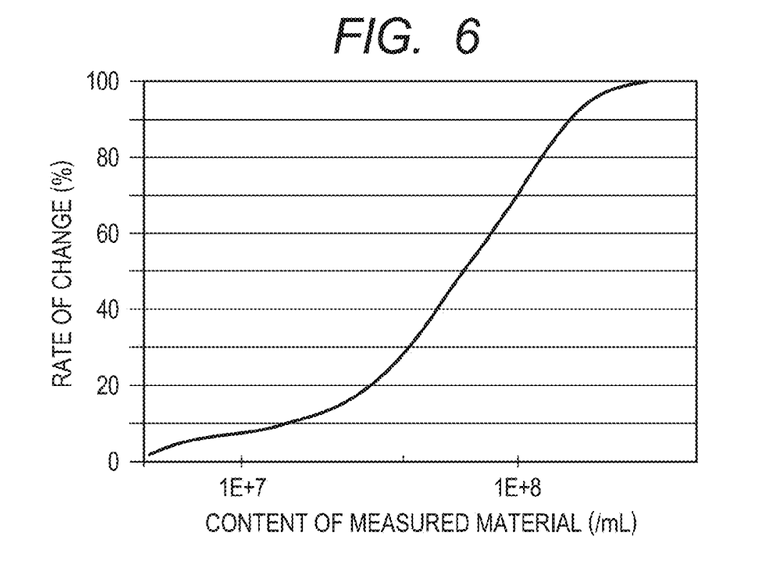
FIG. 6 is a characteristic diagram illustrating an example of a calibration curve acquired in the embodiment.

FIG. 6 is a conceptual diagram illustrating the reaction of the modified embodiment of agglomerating and precipitating a group of magnetic beads by the object to be measured. The sample solution within the sample vessel is added with the magnetic particle 4 with which the antibody 41, and the like, peculiarly coupled with the object to be measured 1 are coupled. This aspect is similar to the embodiment. The group of magnetic particles is coupled and agglomerated via the object to be measured 1 without using the immobilized beads. The agglomerated magnetic particles less follow up the magnetizing AC magnetic field since Brown relaxation time is longer than that of the magnetic particle floating in the solution while being non-coupled. Therefore, when the magnetic particles are sufficiently agglomerated, the magnetic signal strength is reduced, as compared with the magnetic particles floating in the non-coupled state. Further, the exact same method as the immune measuring apparatus illustrated in FIG. 1 of applying the dissociating magnetic field followed by the application of the AC magnetic field for magnetization to promote the precipitation of the coupled magnetic particles and setting the position of the measurement by the magnetizing coil and the magnetic sensor as the upper part of the sample vessel dissociated from precipitates is performed. Therefore, it is possible to suppress the mixing of the magnetic signal from the coupled magnetic particle and effectively measure the quantity of the object to be measured included in the sample solution.

The AC magnetic susceptibility measurement performed in the above embodiment and the modified embodiment is characterized in that the magnetic measurement is performed on the sample vessel itself under the application of the AC magnetic field for excitation by the dissociation and promotion process from the state in which the reacted magnetic particle and the non-reacted magnetic particle are dispersed and mixed within the sample vessel. The dissociation and promotion process is not limited to the process by the application of magnetic field as in the embodiment. Representatively, the dissociation process using a centrifugal force, that is, the centrifugal dissociation may be applied. As in the sample support 13 of the apparatus of FIG. 1, when the sample vessel is arranged and kept in a circumferential shape, a height of the arrangement of the sample vessel deviates from the position of the coil and the sample support rotates at a required rotating speed. In this case, the apparatus may be changed to have a structure in which the lower part of the sample vessel shakes outwardly. Therefore, the dissociation and promotion of the magnetic particle coupled by the centrifugal force may be achieved.

Figure 7:
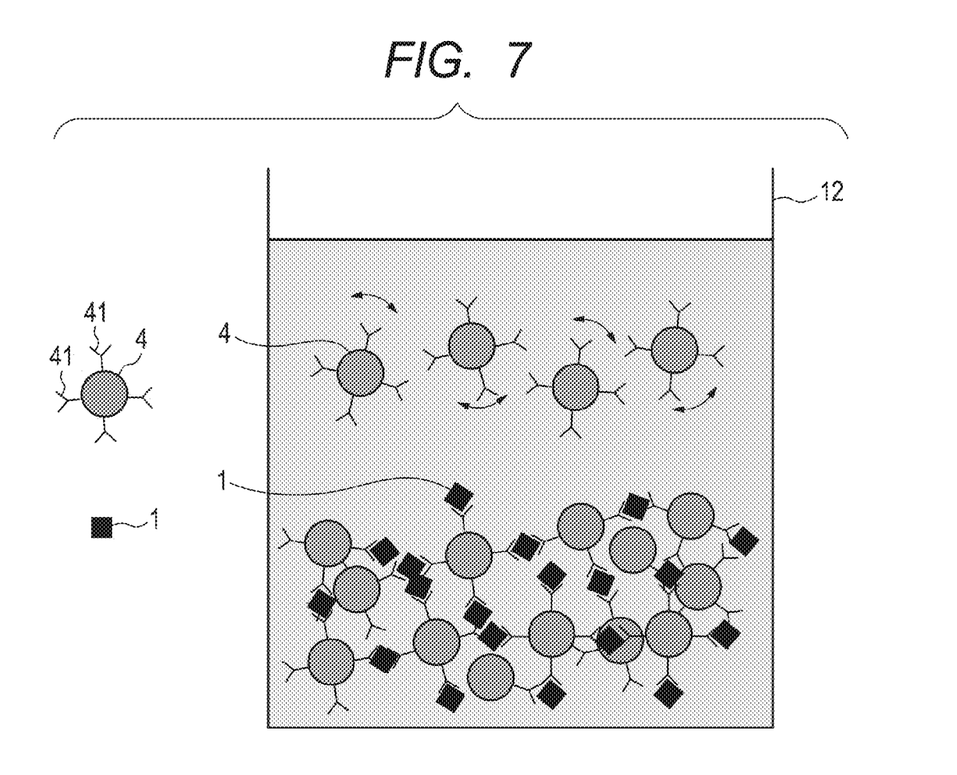
FIG. 7 is a conceptual diagram illustrating a modified embodiment of a dissociating mechanism.
Figure 8:
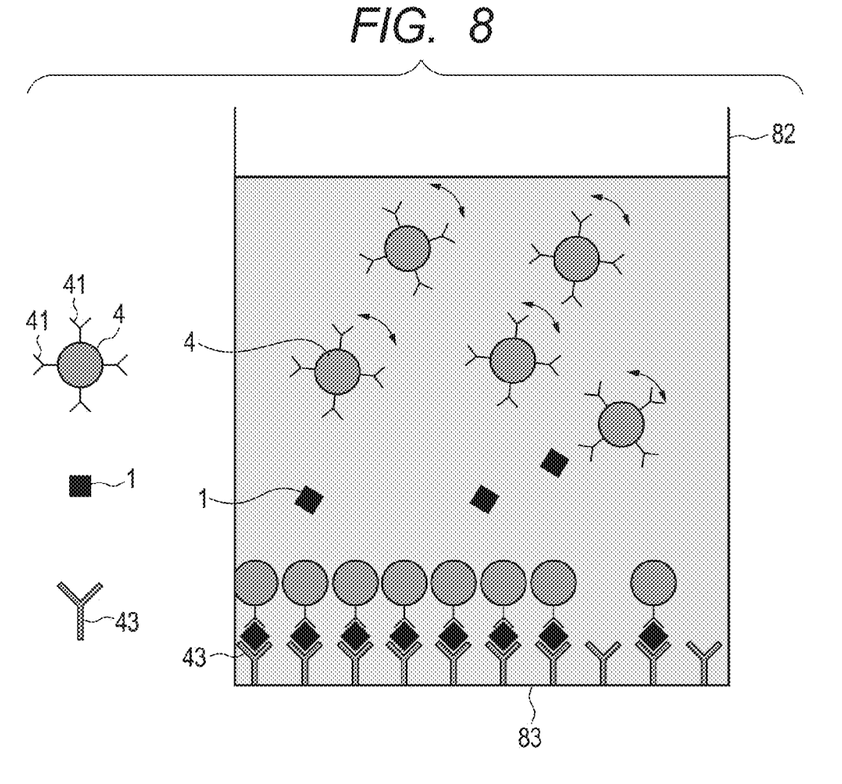
FIG. 8 is a conceptual diagram illustrating another modified embodiment of a dissociating mechanism.

FIG. 7 illustrates a modified embodiment using another dissociation mechanism. The fact that the magnetic particle 4 coupled with the antibody 41, and the like, peculiarly coupled with the object to be measured 1 is added is similar to Example 1 illustrated in FIG. 2 or the modified embodiment illustrated in FIG. 6. In this modified embodiment, a sample vessel 82 in which the second antibody 43 peculiarly coupled with the object to be measured is fixed to a part of the inner wall surface, for example, a bottom surface 83 is used. The magnetic particle 4 is coupled with the second antibody of the wall surface via the antigen that is the object to be measured, and therefore similar to the coupling with the immobilized beads, the Brown relaxation time becomes long and the magnetic particle 4 does not follow up the AC magnetic field for excitation and as a result, the magnetic signal strength is reduced. In order to perform the coupling according to the quantity of antigen that is the object to be measured, the sufficient agitation and reaction time are required. Herein, the application of the dissociating magnetic field and the same magnetic field using in the apparatus of the embodiment or the dissociation process using the foregoing centrifugal force has an effect of promoting the fixing to the wall surface due to the coupling reaction.

Verification of Effect in Embodiment

In order to verify the effect of the measurement according to the configuration of the apparatus according to the foregoing embodiment, the measurement was performed using the following sample. As the magnetic particle, MagCellect streptavidin mark magnetic minute particle (R&D Systems Inc.) commercially available as the purpose of cell dissociation was used. Further, the biotin molecule was selected as the object to be measured.

Instead of adding the object to be measured and the immobilized beads to the solution, a biotin bead in which the biotin is fixed to a polystyrene bead in advance was used (particle size of 3.3 μm, Spherotech, Inc.). These samples were diluted with a phosphate buffer solution and the biotin bead was diluted so that the final concentration of the biotin bead is 1.1e6 to 1.7e7 number/mL. Next, the two samples were mixed and coupled and reacted at 37° C. for one hour (bead sample) Further, the sample of the non-coupled magnetic particle unit of which the number of the object to be measured corresponds to 0 was also diluted similarly and thus was formed as the control sample. After the reaction ends, the bead sample and the control sample are each put in the sample vessel 12 and were each subjected to the magnetic measurement by the immunoassay apparatus of the embodiment. The two settings were performed by the positioning stage 35 so that the position of the MR sensor 15 is the upper part (supernatant measurement) of the vessel and the lower part (precipitation measurement) of the vessel, respectively, at the time of the measurement and the measurement was performed. The strength of the AC magnetic field for excitation was set to be 1 mT or less and the frequency was set to be 10 to 1,000 Hz. By the foregoing Equation 1, in the magnetic signal output of each bead sample, the change rate $\alpha n$ (n=1, 2, 3, . . . ) from the magnetic signal output of the control sample was calculated. When the calculated result is plotted on the two-dimensional plane of which the horizontal axis represents the number of beads of the biotin bead, the results illustrated in FIG. 9 were obtained. A white plot point represents the measured result obtained by disposing the sensor under the vessel.

It may be appreciated that in the region in which the number of beads are many, the change rate representing the reduction degree in the magnetic signal strength from the magnetic signal strength of the control sample (the number of biotin beads is 0) is reduced. The black plot point is the measured result obtained by disposing the sensor above the vessel, and it can be appreciated that as the number of beads of the biotin bead is increased, the reduction degree of the measurement signal is increased, and the change rate is approximately 100% in the sufficient number of beads, that is, the magnetic signal is not substantially measured from the bead sample. The results represents that the mixing of the magnetic signal from the conjugate collected in the lower part of the vessel hinders the extraction of the magnetic signal of the magnetic particle that is non-coupled and floats in a solution and causes a wrong quantifying result, and also represents that in the measuring configuration of the embodiment in which the MR sensor is disposed above the vessel, the mixing of the magnetic signal is excluded from the conjugate, only the signal component may be detected from the magnetic particle that is non-coupled and in a dispersion state, and the quantity of the magnetic particle reduced by the coupling with the object to be measured is accurately reflected.

Figure 9:
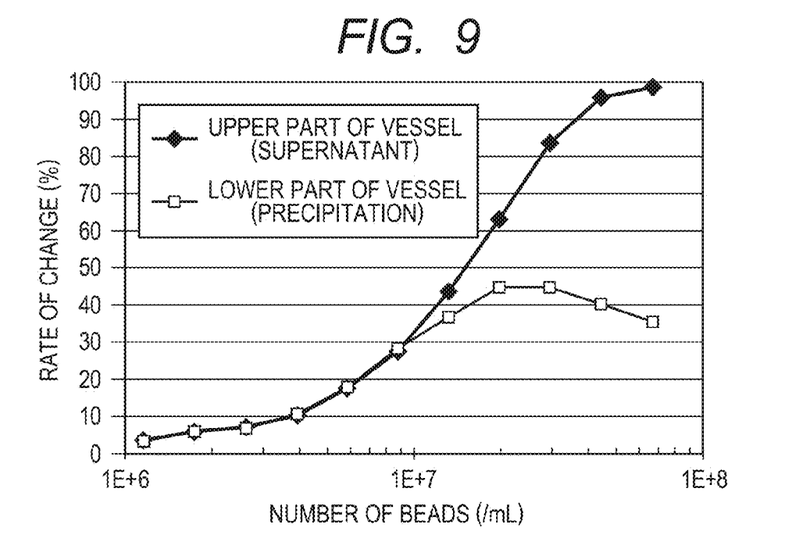
FIG. 9 is a characteristic diagram illustrating results of an experiment verifying effects of the embodiment.
Figure 10:
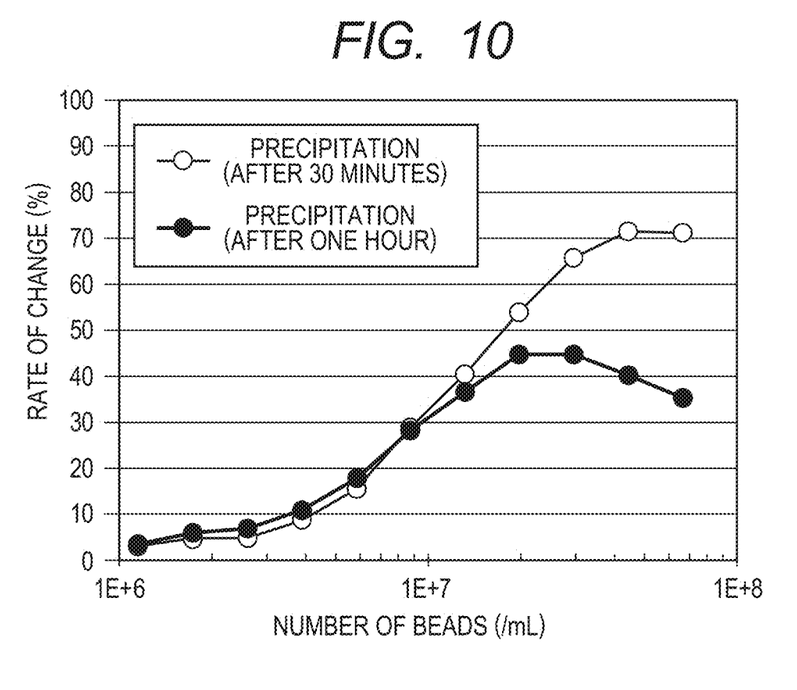
FIG. 10 is a characteristic diagram illustrating results of an experiment (precipitation measurement) verifying the effects of the embodiment.
Figure 11:
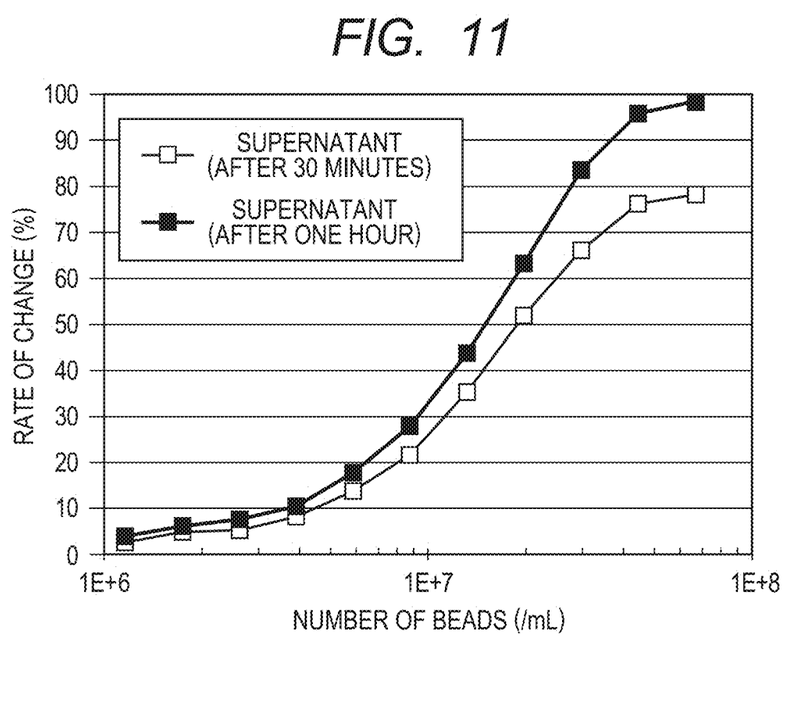
FIG. 11 is a characteristic diagram illustrating results of an experiment (supernatant measurement) verifying the effects of the embodiment.

FIGS. 10 and 11 illustrate the result of the verification experiment reflecting even the change according to the lapse of the reaction time. The plot point represented by a black circle in FIG. 10 corresponds to the measured result (change rate of the magnetic signal strength) obtained by disposing the sensor under the vessel of FIG. 9 and the plot point represented by a white circle corresponds to the change rate of the magnetic signal strength calculated from the measurement of each bead sample performed by similarly disposing the sensor under the vessel and shortening the reaction time to 30 minutes. Further, when there is no mixing of the magnetic signal from the coupled magnetic particle, the change rate from the magnetic signal output of the control sample is increased according to the progress of the coupling reaction, but the result of FIG. 10 represents the change according to the lapse of the reverse time.

In FIG. 11, the black plot point represents the measured results obtained by disposing the sensor above the vessel of FIG. 9 and the black plot point represents the change rate calculated from the measurement of each bead sample performed by similarly disposing the sensor above the vessel and shortening the reaction time to 30 minutes. FIG. 11 illustrates the chronological progress in which the change rate from the magnetic signal output of the control sample is increased according to the progress of the reaction. Comparing the results of FIGS. 10 and 11, the configuration and the measurement sequence of the embodiment of limiting the magnetic measurement range to the sample vessel, promoting the precipitation of the conjugate within the vessel, and then performing the magnetic measurement may exclude the mixing of the magnetic signal from the conjugates and perform the measurement accurately indicating the quantity of the magnetic particle reduced by the coupling with the measured material reflecting only the signal component from the magnetic particle in the dispersion state, thereby realizing the accurate detection and quantification of the measured material.

According to the present invention, in the immunoassay performing the AC magnetic susceptibility measurement, a labor to prepare the sample is shortened, the reliability of the detection is secured, and the precision of the quantification is increased, such that the present invention can be widely used for the fields of the immunoassay technology.

What is claimed is:

1. A magnetic immunoassay method, comprising:
   a first process of mixing a solution assumed as including an object to be measured with a defined quantity of magnetic particle fixed with a first conjugate that binds peculiarly to the object to be measured within a predetermined sample vessel;
   a second process of promoting agglomeration and precipitation of the magnetic particle coupled with the object to be measured within the sample vessel; and
   a third process of magnetizing the solution within the sample vessel with an AC magnetic field and measuring a magnetic signal from a non-coupled magnetic particle remaining in a supernatant of the solution,
   wherein the magnetic particle has a particle size of 200 nm or less,
   whereby the object to be measured is detected and quantified from the obtained magnetic signal strength.

2. The magnetic immunoassay method according to claim 1, wherein in the second process, a dissociating magnetic field is applied to a lower part of the sample vessel.

3. The magnetic immunoassay method according to claim 1, wherein the second process is a process of applying a centrifugal force to the sample vessel.

4. The magnetic immunoassay method according to claim 1, wherein the object to be measured is an antigen and the first conjugate is an antibody.

5. The magnetic immunoassay method according to claim 1, wherein the object to be measured includes an acceptor and the first conjugate is a ligand coupled with the acceptor.

6. The magnetic immunoassay method according to claim 1, wherein the object to be measured is biotin or a material coupled with the biotin as a mark and the first conjugate is avidin or streptavidin.

7. The magnetic immunoassay method according to claim 1, wherein in the first process, immobilized beads fixed with a second conjugate that binds peculiarly to the object to be measured is further mixed in the solution and in the second process, a conjugate of the magnetic particle and the immobilized beads, which are coupled via the object to be measured, is agglomerated and precipitated.

8. The magnetic immunoassay method according to claim 7, wherein the object to be measured is an antigen and the first and second conjugates each are an antibody.

9. The magnetic immunoassay method according to claim 7, wherein the object to be measured is biotin or a material coupled with the biotin as a mark and the first and second conjugates are avidin or streptavidin.

10. The magnetic immunoassay method according to claim 1, wherein the second conjugate that binds peculiarly to the object to be measured is fixed to a wall surface in the vicinity of a bottom of the sample vessel and in the second process, the magnetic particle is fixed to the wall surface of the sample vessel via the object to be measured.

* * * * *